United States Patent [19]
Meinershagen

[11] Patent Number: 4,966,143
[45] Date of Patent: Oct. 30, 1990

[54] SURGICAL WIRE GUIDE

[76] Inventor: Charles I. Meinershagen, P.O. Box 705, Redding, Calif. 96099

[21] Appl. No.: 280,461

[22] Filed: Dec. 6, 1988

[51] Int. Cl.$^5$ .......................................... A61B 17/06
[52] U.S. Cl. .................................. 606/103; 606/223
[58] Field of Search ................... 128/339, 340, 334 R, 128/303 R

[56] References Cited

U.S. PATENT DOCUMENTS

| | | | |
|---|---|---|---|
| 2,833,284 | 5/1958 | Springer | 128/340 |
| 2,897,820 | 8/1959 | Tauber | 128/340 |
| 4,349,027 | 9/1982 | DiFrancesco | 128/303 R |
| 4,392,495 | 7/1983 | Bayers | 128/334 R |
| 4,726,369 | 2/1988 | Mar | 128/303 R |
| 4,784,139 | 11/1988 | Demos | 128/339 |
| 4,803,984 | 2/1989 | Narayanan et al. | 128/334 R |
| 4,819,640 | 4/1989 | Narayanan et al. | 128/334 R |

Primary Examiner—Edward M. Coven
Assistant Examiner—Gary Jackson
Attorney, Agent, or Firm—Townsend and Townsend

[57] ABSTRACT

A surgical wire guide for facilitating the installation of surgical wire around structures to form a ligature. A curved guide has a groove extending along the length thereof and terminates in either a blind, undercut tip portion or an apertured tip portion. A surgical wire is received in the groove and is retained in the tip portion by either the blind undercut or the wall surrounding the aperture. The other end of the guide from the tip end is configured so that the adjacent portion of the surgical wire in the groove can be clamped to the body of the guide by a hand held clamping device. The guide provides a relatively rigid carrier for enabling the surgical wire to be maneuvered through the soft tissue without tearing the tissue and around the structures to be wired.

12 Claims, 1 Drawing Sheet

U.S. Patent
Oct. 30, 1990
4,966,143
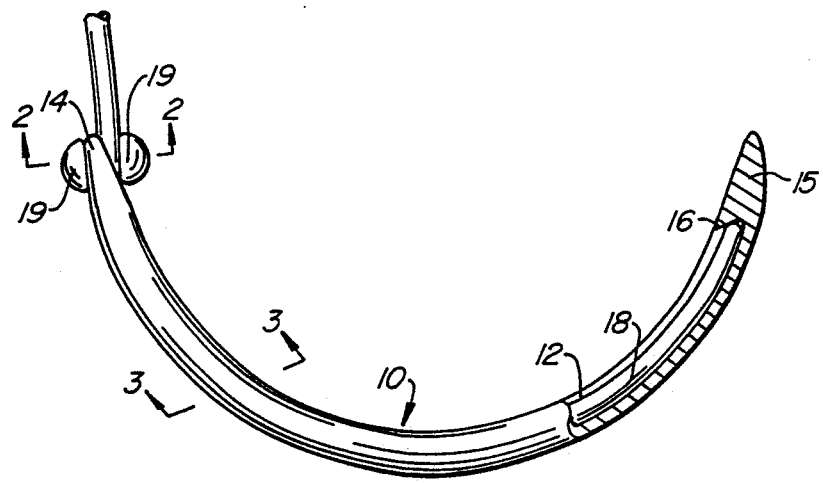
FIG._1.
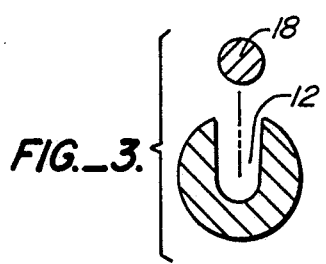
FIG._3.
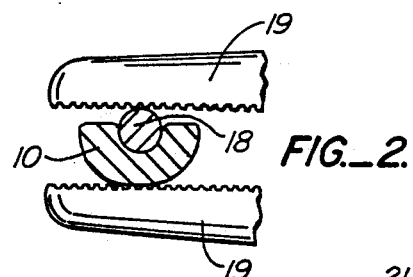
FIG._2.
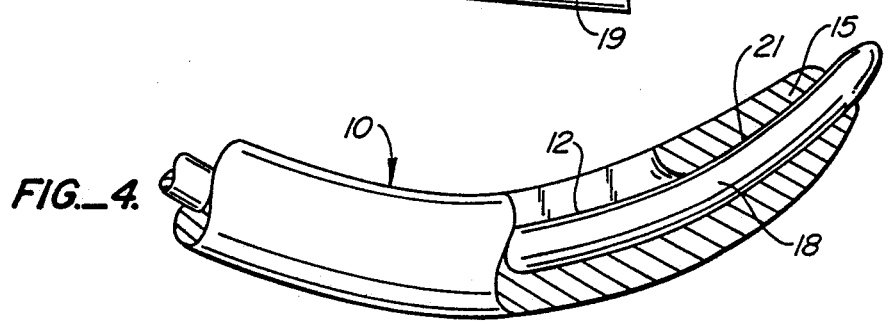
FIG._4.
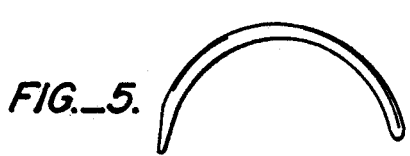
FIG._5.
FIG._6.
FIG._7.

4,966,143

SURGICAL WIRE GUIDE

BACKGROUND OF THE INVENTION

This invention relates to surgical instruments for assisting a surgeon in inserting surgical ligature wire. More specifically, this invention relates to a guide for enabling surgical ligature wire to be inserted quickly, safely and in the exact location desired.

It is often difficult for an orthopedic, oral, neuro or veterinary surgeon to insert stainless steel surgical ligature wire through small holes or around tight, blind corners without puncturing or impaling vital arteries, nerves, or muscle tissue in close proximity to the structures that need to be wired. Many of the instruments for guiding surgical wire that are in use today are either too large and bulky, or require the wire to be bent at a sharp angle which can often catch or lacerate soft tissue. If a surgical ligature wire is inserted by itself, it frequently kinks up, becomes bent, punctures soft tissue structures, or simply ends up in the wrong location.

SUMMARY OF THE INVENTION

The invention comprises a guide for surgical wire which enables a surgeon to insert a surgical ligature wire quickly, safely and in the precise location desired.

The guide comprises an elongate body having a longitudinally extending groove open at one end of the body and terminating at the tip end of the body, the groove having a depth sufficient to accommodate a surgical wire. The guide further includes means at the tip end for retaining the distal end of the surgical wire within the adjacent portion of the groove during manipulation of the guide through the soft tissues around the structures to be wired. In one embodiment of the invention, the retaining means for the wire comprises a portion of the body at the tip end which forms an undercut region adjacent the groove. In another embodiment, the retaining means comprises an aperture formed through the tip portion of the body which receives the distal end of the surgical wire.

The guide further includes means for enabling the surgical wire received in the groove to be fixed or clamped against movement relative to the guide during use. The enabling means comprises either a shallow portion of the body or a shallow portion of the groove, each of which exposes a portion of the surgical wire for clamping by a suitable device, such as a hemostat or a needle holder.

The tip end of the body is preferably tapered in order to assist in penetration of the tissue, and may even include a sharpened point.

The body may be formed in several curved shapes, with different radii of curvature, in order to facilitate manipulation of the guide through the soft tissue around the structures to be wired.

For a fuller understanding of the nature and advantages of the invention, reference should be had to the ensuing detailed description taken in conjunction with the accompanying drawings.

BRIEF DESCRIPTION OF THE DRAWINGS

FIG. 1 is an elevational side view partially broken away illustrating a first embodiment of the invention;

FIG. 2 is a partial sectional view taken along lines 2—2 of FIG. 1;

FIG. 3 is a sectional view taken along lines 3—3 of FIG. 1;

FIG. 4 is an enlarged detailed view of the tip portion of a second embodiment of the invention; and FIGS. 5-7 are side elevational views of three specific embodiments having different radii of curvature.

DESCRIPTION OF THE PREFERRED EMBODIMENTS

Turning now the drawings, FIG. 1 illustrates a first embodiment of the invention. As seen in this Fig., a curved body generally designated with reference numeral 10 has a longitudinally extending groove 12 beginning at a first beveled end 14 and terminating adjacent a tip portion 15. Groove 12 terminates within the body of guide 10 adjacent an undercut wall portion 16, which serves to retain the tip of a length of surgical wire 18 shown received within groove 12.

As best seen in FIG. 2, end 14 of guide 10 has a reduced diameter so that the wire 18 can be clamped to the body of the guide 10 by means of a suitable clamping mechanism, illustrated in FIG. 2 as the beaks 19 of a conventional hemostat. Other suitable clamping devices, such as a conventional needle holder, will occur to those skilled in the art.

As best seen in FIG. 3, the depth of groove 12 formed in the body of guide 10 is sufficiently great to accommodate the diameter of wire 18, so that wire 18 may nest completely within the groove 12 upon installation. Guide 10 is preferably fabricated from a stainless steel material, with the groove 12 being formed in any suitable way known to those skilled in the art, such as by scoring, milling, or the like.

In use, the surgical wire 18 is bent to generally conform to the curvature of the guide 10, after which the tip end of wire 18 is inserted adjacent tip portion 15 of guide 10 so that the tip of the wire 18 is retained by means of the undercut solid wall surface 16. Thereafter, the wire 18 is maneuvered into the groove 12 all along the length of guide 10, after which a portion of the wire 18 adjacent end 14 is gripped by the beaks 19. Thereafter, the tip of the guide is maneuvered into the soft tissue around the structures to be wired together, while firmly clamping wire 18 by means of the beaks 19 so that the wire 18 and the guide 10 are maneuvered as a unit through the tissue. Once the guide 10 has been sufficiently maneuvered around the structure to be wired, the beaks 19 are released so that the guide 10 can be pulled the rest of the way through the tissue and removed from the surgical area, leaving the wire in the desired location. In order to assist in the penetration of the guide through the soft tissue, tip portion 15 is tapered as shown in FIG. 1. In addition, if desired, tip portion 15 may terminate in a sharpened point.

FIG. 4 illustrates an alternate embodiment of the invention in which the means for retaining the tip of the wire 18 in the guide 10 comprises an aperture 21 extending from the termination of the groove 12 through the tip 15 of the guide 10. In this embodiment, the free end of the wire 18 is initially maneuvered via aperture 21 through the tip 15 to the slightly protruding position illustrated in FIG. 4. Thereafter, use of the FIG. 4 embodiment proceeds as already described with reference to the embodiment of FIGS. 1-3.

FIGS. 5-7 illustrate alternate curved shapes for the body 10, with the curvature of FIG. 5 being the sharpest and the curvature of FIG. 7 being the slightest.

Other curved shapes will occur to those skilled in the art.

As will now be apparent, the invention affords a ready solution to the problem of maneuvering surgical wire through soft tissue around structures to be wired. The relative stiffness of the guide 10 enables sufficient force to be applied through the clamping mechanism so that the surgeon can readily maneuver the guide through the soft tissue around the structures. In addition, since the tip of the wire 18 is entirely encased within the tip portion of the guide (in the FIG. 1 embodiment) or protrudes only slightly from the tip portion 15 of the guide (in the FIG. 4 embodiment), the wire will not kink or tear the soft tissue as it is being manipulated therethrough.

While the above provides a complete description of the preferred embodiments of the invention, various modifications, alternate constructions, and equivalents will occur to those skilled in the art. For example, if desired, the depth of the groove 12 can be reduced so that the surface of the wire 18 protrudes slightly beyond the wall of the body 18. In addition, the tip portion 15 may be modified so that the groove 12 extends along the entire length of the guide 10 and the retaining function is performed by crimping together the side walls of the groove 12 at the tip 15. Also, other curved shapes than those illustrated may be employed, as desired. Therefore, the above should not be construed as limiting the invention, which is defined by the appended claims.

What is claimed is:

1. A guide for surgical wire comprising an elongate body having a longitudinally extending groove open at one end of the body and terminating at the tip end of the body, said groove having a depth sufficient to accommodate a surgical wire, and means comprising a solid portion of said body with an undercut formed adjacent said tip end for retaining the distal end of the surgical wire within the adjacent portion of said groove.

2. The invention of claim 1 wherein said tip portion of said body is provided with an aperture to receive the distal end of the surgical wire, and said retaining means includes a solid portion of said tip portion adjacent said aperture.

3. A surgical wire guide for facilitating the installation of surgical wire in tissue to form a ligature, said guide comprising an elongate body having a longitudinally extending groove beginning at a first end of said body and extending to a tapered tip portion of said body, said groove terminating adjacent the tip portion in a blind bore having an undercut wall portion adjacent said up portion to assist in retaining the tip of a length of surgical wire received in said groove, and means for enabling the surgical wire to be clamped to the body to prevent relative movement therebetween during use of said guide.

4. The invention of claim 3 wherein said enabling means comprises a reduced wall portion of said body for exposing a portion of the surgical wire.

5. The invention of claim 3 wherein said enabling means comprises a shallow groove portion for exposing a portion of the surgical wire.

6. The invention of claim 3 wherein said body is curved.

7. A surgical wire guide for facilitating the installation of surgical wire in tissue to form a ligature, said guide comprising an elongate body having a longitudinally extending groove beginning at a first end of said body and extending to a tapered tip portion of said body, said groove communicating with an aperture formed in the tip portion of said body and dimensioned to receive the distal end of a length of surgical wire when received in said groove, and means for enabling the surgical wire to be clamped to the body to prevent relative movement therebetween during use of said guide.

8. The invention of claim 7 wherein said enabling means comprises a reduced wall portion of said body for exposing a portion of the surgical wire.

9. The invention of claim 7 wherein said enabling means comprises a shallow grooved portion for exposing a portion of the surgical wire.

10. The of claim 4, 5, 8 or 9 wherein said enabling means is located adjacent the first end of said body.

11. The invention of claim 7 wherein said body is curved.

12. A guide for surgical wire comprising an elongate body having a longitudinally extending groove open at one end of the body and terminating at the tip end of the body, said groove having a depth sufficient to accommodate a surgical wire, and means at said tip end for retaining the distal end of the surgical wire within the adjacent portion of said groove, said body having a tip portion provided with an aperture to receive the distal end of the surgical wire, said retaining means including a solid portion of said tip portion adjacent said aperture.

* * * * *